United States Patent

Kim et al.

[11] Patent Number: 6,156,344
[45] Date of Patent: Dec. 5, 2000

[54] METHOD FOR IMPROVING BLOOD COMPATIBILITY OF INTERPENETRATING MULTICOMPONENT POLYMER

[75] Inventors: Sung-Chul Kim, Seoul; Yong-Cheol Shin; Hyang-Woo Roh, both of Kyunggi-Do; Mi-Jeong Song, Taejon, all of Rep. of Korea

[73] Assignee: Korea Advanced Institute of Science and Technology, Taejon, Rep. of Korea

[21] Appl. No.: 08/996,523

[22] Filed: Dec. 23, 1997

[30] Foreign Application Priority Data

Dec. 26, 1996 [KR] Rep. of Korea ..................... 96-72482

[51] Int. Cl.$^7$ ............................ C08L 75/04; A61L 27/00; A61F 2/06
[52] U.S. Cl. ................................ 424/484; 623/11; 623/12
[58] Field of Search ..................................... 424/486, 484

[56] References Cited

U.S. PATENT DOCUMENTS 4,302,553 11/1981 Frisch et al. .
5,395,888 3/1995 Franke et al. .

OTHER PUBLICATIONS

Advances in Chem. Series (239/1994 ACS Interpenetrating Polymer Networks pp. 28–31, 307–309 Ed. Klempner et al. T. Okano et al J. of Biomedical Research, vol. 20, 919–927 (1986).

T. Okano et al., Hydrophilic–hydrophobic Microdomain Surfaces Having an Ability to Supress Platelet Aggregation and Their in vitro Antithrombogenicity, J. Biomed. Mater. Res., 20, 919–927 (1986).

Y.H. Kim et al., Negative Cilia Concept for Thromboresistance: Synergistic effect of PEO and Sulfonate Groups Grafted onto Polyurethanes, J. Biomed. Mater. Res., 25, 561–575 (1991).

*Primary Examiner*—Peter F. Kulkosky
*Attorney, Agent, or Firm*—Knobbe Martens Olson & Bear, LLP

[57] ABSTRACT

The present invention provides a method for improving blood compatibility of interpenetrating multicomponent polymer by controlling various factors affecting phase separation such as composition ratio, synthetic temperature, synthetic pressure, cross-linking density and hydrophilicity of polyurethane in the course of synthesizing interpenetrating polymer network ("IPN") where hydrophilic urethane resin and hydrophobic styrene derivative are cross-linked each other. IPN materials of the invention may be widely used in various applications such as artificial organ or surface finishing material which are in direct contact with blood, since they inhibit thrombogenesis by suppressing platelet adhesion and agglutination.

16 Claims, 3 Drawing Sheets

METHOD FOR IMPROVING BLOOD COMPATIBILITY OF INTERPENETRATING MULTICOMPONENT POLYMER

FIELD OF THE INVENTION

The present invention relates to a method for improving blood compatibility of interpenetrating multicomponent polymer, more specifically, to a method for improving blood compatibility of interpenetrating multicomponent polymer by controlling various factors affecting phase separation such as composition ratio, synthetic temperature, synthetic pressure, cross-linking density and hydrophilicity of polyurethane, in the course of synthesizing of interpenetrating polymer network where hydrophilic urethane resin and hydrophobic styrene derivative are cross-linked each other.

BACKGROUND OF THE INVENTION

Among multicomponent polymers, an interpenetrating polymer network ("IPN") is the sole macromolecule synthesized through cross-linking, which is a mixture of more than two macromolecular, physically interwound cross-linked structure, having different characteristics such as hydrophilicity/hydrophobicity. So far, it has been reported that an IPN with hydrophobicity/hydrophobicity has a sea-island phase separation structure with excellent properties, which can be controlled to be a co-continuous morphology by changing synthetic temperature or pressure (see: S. S. Lee and S. C. Kim, Polymer (Korea), 10(3);236(1986); S. K. Kim and S. C. Kim, Polymer Bulletin, 23:141(1990)). Accordingly, on the ground that the IPN with hydrophilicity/hydrophobicity has excellent material properties and its hydrophilic/hydrophobic phase separation structure shows blood compatibility, it has been proposed as a promising biomaterial used for the direct contact part with blood.

The IPN can be prepared by the following two polymerization methods: Sequential polymerization method comprises the steps of synthesizing a cross-linked macromolecule A, and allowing polymerization and cross-linking of monomer B in a swelled macromolecule A; and, simultaneous polymerization method comprises the steps of mixing monomer A and B, non reactive each other (e.g., A is a monomer cross-linked through the reaction of free radical by double bond, while B is a monomer condensate-polymerized through functional reaction at the end of B), and synthesizing cross-linked macromolecules A and B in a simultaneous and independent manner. In the IPN, more micro dispersion state can be obtained, since cross-linking structures of two macromolecules are physically interwound to inhibit further phase separation, when polymerization of monomers reaches at the gelation point. Further, spinodal or co-continuous structure can be obtained, if the phase separation is suppressed in the early stage.

In general, phase separation occurs at multicomponent polymers, since polymers with more than two different properties are linked each other. This phase separation is a critical factor affecting properties of material, which is affected mainly by chemical structure, composition and manufacturing process of macromolecules. Also, IPN, a multicomponent polymer, shows a phase separation structure which is controlled by miscibility, cross-linking density, reaction velocity, mobility of macromolecular chain, etc.

On the other hand, there have been attempts to develop materials inhibiting thrombogenesis, since antithrombogenecity is the most important characteristic in the field of artificial blood vessel which is directly contacted with blood. The macromolecular surface affecting blood compatibility is changed largely by physical and chemical structure. In this connection, studies on blood compatibility have been actively carried out in light of polarity, surface energy, degree of hydrophilicity/hydrophobicity and so on. When the macromolecular surface comes to contact with blood, thrombus is finally formed on the surface. Although the process of thrombogenesis is not clearly known at present, it is generally accepted that when macromolecular surface comes to contact with blood, plasma protein immediately adsorbs on the surface and the adsorbed protein interacts with platelet, which is directly or indirectly related with the thrombogenesis through agglutination of platelet, modification and aggregation. In short, the macromolecular characteristic plays a very important role in interaction of macromolecule, which accelerates the studies on the effect of hydrophilicity/hydrophobicity of the macromolecular surface.

For example, U.S. Pat. Nos. 4,687,831 and 4,675,361 disclosed the use of block co-polymer in the linking of hydrophilicity and hydrophobicity and hard and soft chain. Also, Okano et al. reported that blood compatibility of block co-polymer consisted of hydrophilic poly(2-hydroxyethyl methacrylate) and hydrophobic polystyrene is related with the composition change of the hydrophilic component (see: T. Okano et al., J. Biomed. Mater. Res., 15:393)1982)). Moreover, Shimada et al. reported the blood compatibility depending on the composition change of block co-polymer of hydroxyethylmethacrylate-dimethylsiloxane (see: M. Shimada et al., Polymer J., 15:649(1983)).

However, the conventional hydrophilic/hydrophobic block co-polymers have been proven to be less satisfactory in a sense that they do not provide sufficient blood compatibility in light of mechanical properties and maintenance of phase separation structure.

In this regard, the inventors have tried to improve the blood compatibility, based on Okano et al's hypothesis that blood compatibility of the hydrophilic/hydrophobic microphase separation surface is closely related with the selective adsorption of plasma protein on the macromolecular surface (see: T. Okano et al., J. Biomed. Mater. Res., 15:393(1981)). Antithrombogenesis by the selective adsorption of plasma protein on the macromolecular surface has a significance that: among plasma proteins, albumin comes to be adsorbed on the hydrophilic part, while fibrinogen and gamma-globulin comes to be adsorbed on the hydrophobic part, and the adsorbed plasma protein becomes the textured structure controlled by the hydrophilic/hydrophobic microphase structural surface, which results in the inhibition of activation of platelet. In this regard, the factors affecting agglutination and activation of platelet in the hydrophilic/hydrophobic microphase structure are the balance of hydrophilicity and hydrophobicity in the macromolecular surface and the morphology and the size of hydrophilic/hydrophobic microphase. Actually, normal epithelial cells of blood vessel having ideal antithrombogenesis have the microphase separation structure consisted of hydrophilicity/hydrophobicity.

Accordingly, there are strong reasons for exploring and developing a method for improving the blood compatibility of polymers by controlling various factors affecting the platelet agglutination.

SUMMARY OF THE INVENTION

In this regard, the present inventors have made an effect to develop a method for improving blood compatibility of multicomponent polymers, and they synthesized an interpenetrating polymer network (IPN) which has increased antithrombogenesis and decreased phase separation of macromolecular mixture, through cross-linking of hydrophilic urethane resin and hydrophobic styrene derivatives under a proper composition ratio of the two components, a low synthetic temperature, a high synthetic pressure, a high cross-linking density and other enabling the synthesis of polyurethane with increased hydrophobicity on co-polymerization at IPN step polymerization.

A primary object of the present invention is, therefore, to provide a method for improving blood compatibility of an interpenetrating polymer network (IPN), by controlling domain size and inhibiting phase separation of macromolecular mixture in the course of synthesizing an IPN through cross-linking of a hydrophilic urethane resin and a hydrophobic styrene derivative.

BRIEF DESCRIPTION OF DRAWINGS

The above and the other objects and features of the present invention will become apparent from the following description given in conjunction with the accompanying drawings, in which.

DETAILED DESCRIPTION OF THE INVENTION

Figure 1A:
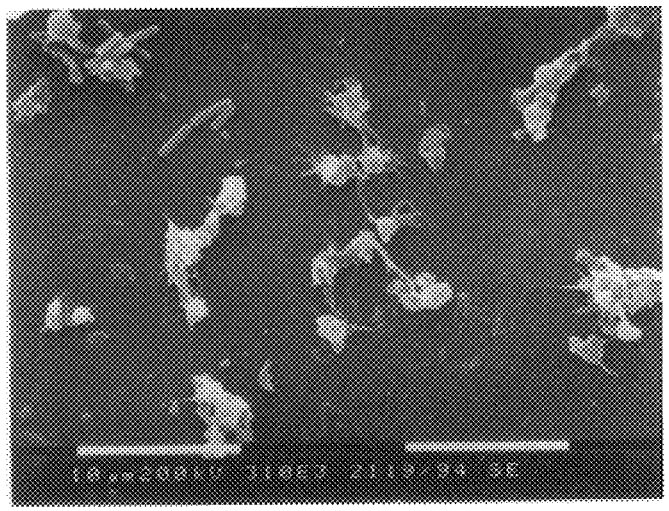
FIG. 1(A) is a SEM micrograph showing platelet adhesion on the surface of IPN whose mean chain length between chains (Mc) is 1,800.

The present invention improved the blood compatibility of an IPN by controlling domain size and inhibiting phase separation of macromolecular mixture, in the course of synthesizing an IPN through cross-linking of a hydrophilic urethane resin of formula (I) and a hydrophobic styrene derivative of formula (II);

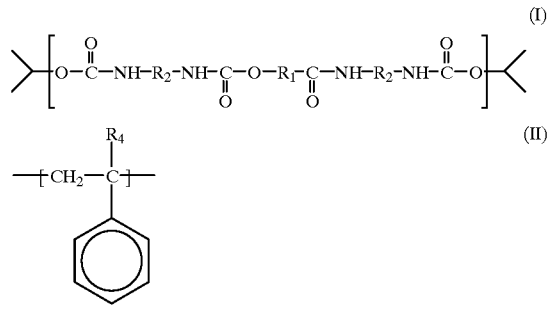

wherein, $R_1$ is $-[-(CHR_3-CH_2-)_n-O-]_m-$ (where, $R_3$ is hydrogen or methyl; n is an integer of 1 to 3; and, m is an integer of 4 to 40);

$R_2$ is $-(-CH-)_n-$ (where, n is an integer of 2 to 8); and, $R_4$ is hydrogen or methyl.

In the method for improving biocompatibility of an IPN, the controlling of domain size and the inhibition of phase separation are realized by controlling composition ratio of two macromolecules, synthetic temperature, synthetic pressure, cross-linking density and degree of hydrophilicity of polyurethane. Preferably, polyurethane component contained in IPN is adjusted to be 20 to 80%, synthetic pressure to be 1 to 10,000 atmospheric pressure, mean chain length of each macromolecule network to be 600 to 3000 and hydrophobicity of polyurethane to be increased by introducing more than two kinds of $R_1$ substituents with different hydrophilicity to polyurethane.

In practicing the present invention, IPN may be synthesized by one of following two methods: simultaneous polymerization method of fabricating polyurethane and polystyrene at 40 to 150° C.; and, sequential polymerization method of fabricating polystyrene network after fabricating polyurethane network, where polystyrene network is fabricated by UV photopolymerization at −40 to 50° C.

The urethane-styrene IPNs thus synthesized have been proved to have an excellent properties and an increased blood compatibility, when are tested in accordance with the method described below. Since the IPN materials inhibit thrombogenesis by suppressing adhesion and agglutination of platelet in contact with blood, they can be widely used in various application such as artificial organ and surface finishing material directly contacted with blood.

EVALUATION OF BLOOD COMPATIBILITY

Three kinds of methods are employed to evaluate blood compatibility of follows; in vitro evaluation, in vivo evaluation and ex vivo evaluation.

In vitro evaluation method which measures through a direct contact of blood with material, has been widely used due to its easiness and rapidness. Among these, these are three kinds of platelet measuring methods as follows: a method of analyzing the number of platelet by a platelet counter, after contacting with the surface of material; a method of observing the morphology of platelet adhered to the surface of material; and, a method of counting the number of platelet adhered to a sufficient specimen by micrograph.

In vivo evaluation method actually observes the complicated in vivo coagulation actually. Vena cave ring method observed the coagulated state occurred, after injecting macromolecule into venae cava of dog for a time as a form of ring. The method, however, has a shortcoming that the process of coagulation cannot be continuously observed, although the coagulated state after a specified time may be observed.

As an alternative of in vivo evaluation method, ex vivo evaluation method which measures the coagulation process ex vivo, has been developed. Ex vivo evaluation methods includes the followings: a method of measuring the temperature increase arising from coagulation by installing a cross thermocouple into a catheter; a method of measuring the amount of hemokinesis inside of a ring by a ultrasound flowmeter; A-V (arterio-venuous) shunt method which measures through a macromolecule tube injected between left jugular venous and right arteriae aorta of an animal; and, newly developed A-A (arterio-arterial) shunt method which improved the A-V method by shortening the time required for experiment and minimizing the phase change of blood components.

The present invention is further illustrated by the following examples, which should not be taken to limit the scope of the invention.

EXAMPLE 1

Synthesis of Hydrophilic Urethane Prepolymer

Urethane prepolymer having an iscoyanate (—NCO) terminal was synthesized at a temperature of 60° C. by mixing hexamethylene diisocyanate (hereinafter, referred to as 'HDI') and polyethylene glycol having a molecular weight of 200, 600 or 1,000 (hereinafter, referred to as 'PEG') or polytetramethylene etherglycol having a molecular weight of 1,000 (hereinafter, referred to as 'PTMG') at an equivalent ratio of 2:1 and adding a catalyst, 0.05 wt % of dibutyltin dilaurate (hereinafter, referred to as 'T-12'). At this time, prepolymer was synthesized under a nitrogen environment to prevent the reaction with moisture present in the atmosphere. The reaction was continued to reach to a theoretical value ±5% and terminated after confirming by titration with di-n-butylamine.

EXAMPLE 2

Synthesis of Polyurethane and Polystyrene Network

To synthesize hydrophilic polyurethane, urethane prepolymer synthesized in Example 1 and a mixture of trimethylol propane (hereinafter, referred to as 'TMP')/1,4-butanediol (at an equivalent ratio of 4:1) were mixed at an equivalent ratio of 1:1 and 0.05 wt % T-12, a catalyst, was added to the mixture. After removing the air under vacuum, the mixture was injected between two glass slides and reacted at 80° C. for 48 hours to prepare polyurethane.

Meanwhile, hydrophobic polystyrene was synthesized in an analogous manner as in the above, with the except that 5 wt % of divinylbenzene was employed as a cross-linking agent and 1 wt % of benzoyl peroxide as an initiator, respectively, and mixed with styrene monomer.

EXAMPLE 3

Synthesis of Urethane-Styrene IPNs Containing Various Styrene Composition and Evaluation of Their Blood Compatibility Hydrophilic polyurethane-hydrophobic polystrene IPN was synthesized by mixing simultaneously polyurethane and polystyrene synthesized in Example 2 and reacting under the same conditions as in Example 2. At this time, urethane-styrene INPs containing 30, 50 and 70 wt % styrene component were obtained, respectively, changing the weight ratio of hydrophilic/hydrophobic component while mixing.

To measure the blood compatibility of the urethane-styrene IPNs thus obtained, protein adsorption, platelet adhesion and ex vivo A-A shunt were investigated as followings: Since the interaction of blood cell and macromolecular surface is affected by the behavior of protein adsorbed on the surface, protein adsorption of the IPNs was found to be decreased than that of single component of urethane or styrene. Also, the platelet adhesion measurement revealed that all IPNs of various styrene composition showed less platelet adhered thereto and fewer modification of platelet than that of single component of urethane or styrene. Furthermore, ex vivo A-A shunt experiment employing a tube with 2.0 mm of outer diameter, 1.5 mm of inner diameter and 30 cm of length made of IPNs containing 50 wt % urethane and 50 wt % styrene ("Urethane-Styrene 50/50 IPN") synthesized as above, showed that occlusion time was longer than other biomaterials, which means that blood compatibility of urethane-styrene IPN is superior to other biomaterial currently used, especially to Biomer (see; Table 1).

TABLE 1

Occlusion time of various biomaterials

| Materials | Occlusion time (min) |
|---|---|
| Polystyrene* | 26 ± 0 |
| Biomer* | 45 ± 17 |
| Polyurethane | 50 ± 5 |
| Urethane-Styrene 50/50 IPN | 100 ± 10 |

*Excerpted from C. Nojiri et al., Trans. Am. Soc. Artif. Intern. Organs., 33:596 (1987)

EXAMPLE 4

Change of Blood Compatibility Depending on the Synthetic Temperature of Urethane-Styrene IPN 50% of urethane component comprising urethane prepolymer, a mixture of TMP/1,4-butanediol (equivalent ratio=4:1) and T-12, and 50 wt % of styrene component comprising 5 wt % of divinyl benzene and styrene monomer containing 0.5 wt % of benzoin, were injected into between glass slides and reacted at 50° C. for 8 hours to synthesize polyurethane network. And then, UV photopolymerization was carried out by subjecting the glass slides at the temperatures of 50, 20, 0 or −20° C. for 48 hours under a cold polymerizer equipped with UV lamp ($I_{max}$ wavelength=350 nm) to synthesize styrene network specimen. Table 2 below showed occlusion time by ex vivo A-A shunt test of IPN containing 50% of styrene synthesized at the various different temperatures.

TABLE 2

Occlusion time by ex vivo A-A shunt test of IPN specimen synthesized at various temperatures

| IPN specimen | Occlusion time (min) |
|---|---|
| Urethane-Styrene 50/50 IPN (80° C.)[a] | 100 ± 10 |
| Urethane-Styrene 50/50 IPN (50° C.)[b] | 109 ± 6 |
| Urethane-Styrene 50/50 IPN (20° C.)[b] | 113 ± 10 |
| Urethane-Styrene 50/50 IPN (0° C.)[b] | 119 ± 9 |
| Urethane-Styrene 50/50 IPN (−20° C.)[b] | 125 ± 6 |

[a]temperature in parenthesis is synthetic temperature of heat-polymerization of styrene network.
[b]temperature in parenthesis is synthetic temperature of UV photopolymerization of styrene network.

As shown in the Table 2 above, occlusion time was found to be longer than Biomer of Table 1, which illustrates the improvement of blood compatibility. Also, in vitro platelet adhesion experiment demonstrated that, as synthetic temperature of IPN decreases, adhesion or modification of platelet decreases. Accordingly, the lowering of synthetic temperature on photopolymerization of styrene effectively improves blood compatibility of the synthesized material.

EXAMPLE 5

Change of Blood Compatibility Depending on the Synthetic Pressure of Urethane-Styrene IPN IPN specimen was synthesized in an analogous manner as in Example 3, whose styrene composition is fixed as 50%. At this time, glass slides were replaced with stainless steel fabricated for the use at high pressure, and specimen was synthesized at various pressure of 1,000, 3,000 and 5,000 atmospheric pressure, respectively. Platelet adhesion of the IPNs thus synthesized were summarized in Table 3 below.

TABLE 3

The number of platelet adhered to the surface of urethane-styrene IPN synthesized at the high pressures (unit: platelet number/mm²)

| Specimen (*) | Incubation (3 hours) | Incubation (10 hours) |
|---|---|---|
| TX1000 | 510 | 526 |
| TX3000 | 296 | 480 |
| TX5000 | 110 | 222 |

*: T means that polyurethane, one of components of IPN, is fabricated from prepolymer synthesized by employing polytetramethylene ether glycol (PTMG).
X means that molecular weight of PTMG is 1,000.
Number expresses the pressure at which the specimen is synthesized.

As shown in Table 3 above, it was clearly demonstrated that, as phase separation is inhibited by the increase of synthetic pressure, the number of platelet adhere to the surface of specimen decreases, which means that the blood compatibility is effectively improved.

EXAMPLE 6

Change of Blood Compatibility Depending on the Cross-Linking Density of Urethane-Styrene IPN Polyurethane was synthesized by mixing each of urethane prepolymer (PEG1000, PEG600, PEG200) and a mixture of TMP/1,4-butanediol (equivalent ratio=4:1) at an equivalent ratio of 1:1 and adding 0.05 wt % of T-12. Also, polystyrene was synthesized from styrene monomer, 5 wt % of divinyl benzene and 0.5 wt % of benzion. At this time, mean chain length (Mc) of IPN was adjusted to be 1800, 1300 and 800, respectively.

Specimen was prepared by fabricating urethane network by mixing the two macromolecular mixture at a weight ratio of 1:1, removing gas under vacuum and reacting at 50° C. for 5 hours after injecting between glass slides, by fabricating styrene network through photopolymerization by maintaining the glass slides at −25° C. for 48 hours under a cold polymerizer equipped with UV lamp ($I_{max.}$ wavelength=350 nm), and then strengthening by subjecting at 50° C. for 5 hours and at 100° C. for 2 hours. The blood compatibility of the resulted specimen was evaluated by platelet adhesion test, whose results are shown in FIGS. 1(A) to 1(C).

Figure 1B:
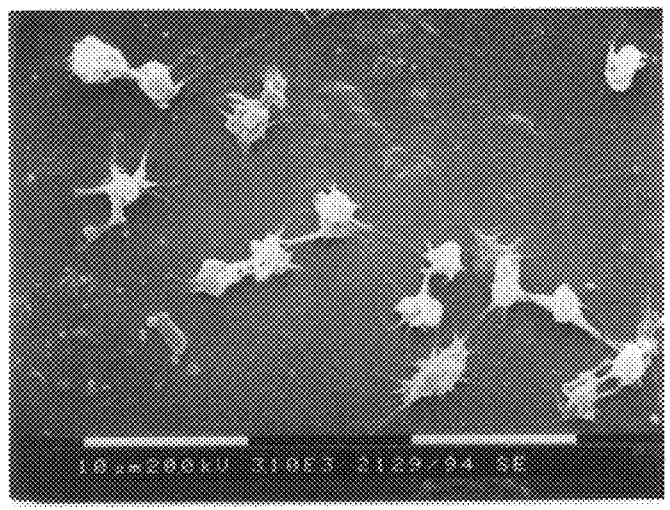
FIG. 1(B) is a SEM micrograph showing platelet adhesion on the surface of IPN whose mean chain length between chains (Mc) is 1,300.
Figure 1C:
FIG. 1(C) is a SEM micrograph showing platelet adhesion on the surface of IPN whose mean chain length between chains (Mc) is 800.
Figure 2A:
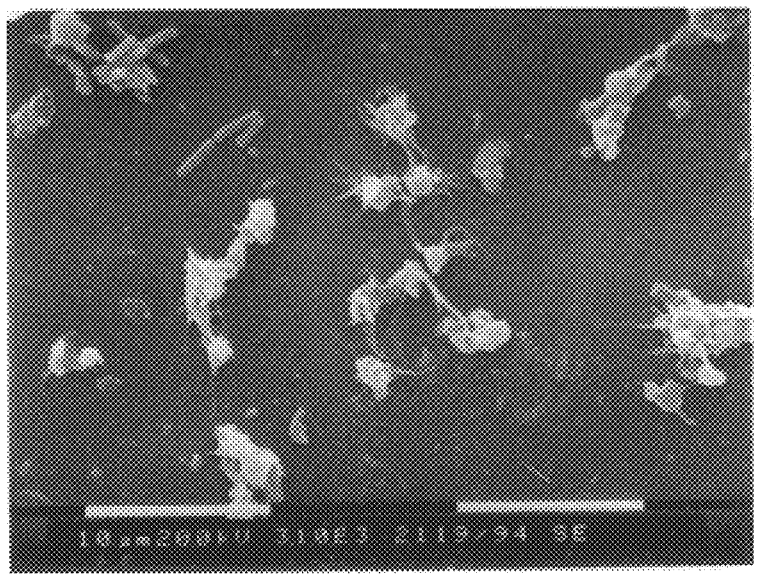
FIG. 2(A) is a SEM micrograph showing platelet adhesion on the surface of urethane-styrene IPN sythesized from a mixture of polyethylene glycol 1000 and polytetramethylene ether glycol 1000 (1:0).
Figure 2B:
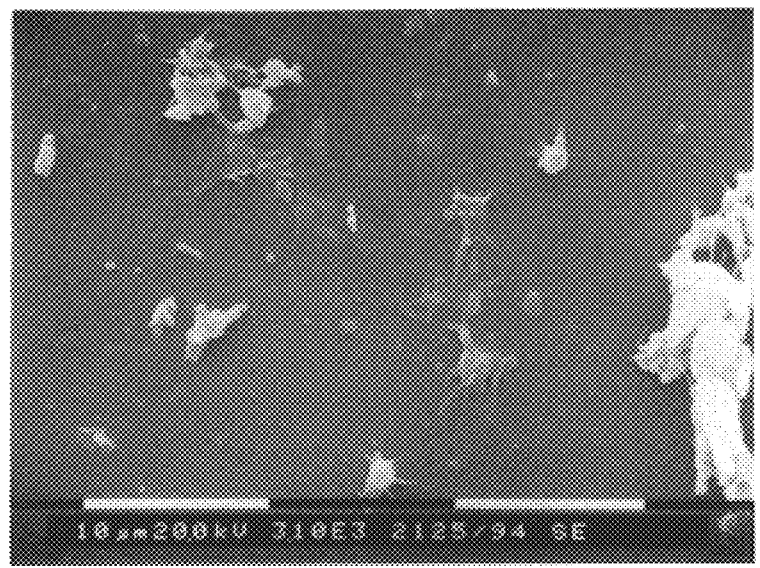
FIG. 2(B) is a SEM micrograph showing platelet adhesion on the surface of urethane-styrene IPN synthesized from a mixture of polyethylene ether glycol 1000 (2:1).
Figure 2C:
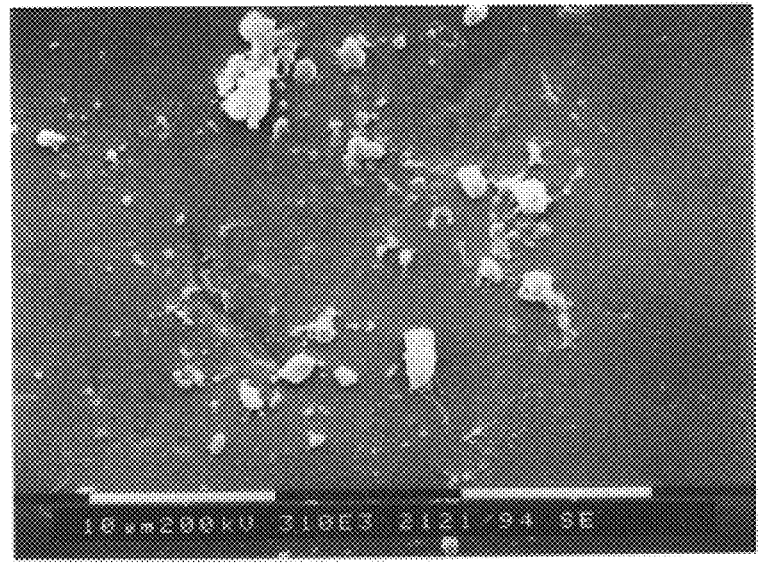
FIG. 2(C) is a SEM micrograph showing platelet adhesion on the surface of urethane-styrene IPN synthesized from a mixture of polyethylene glycol 1000 and polytetramethylene ether glycol 1000 (1:2).
Figure 2D:
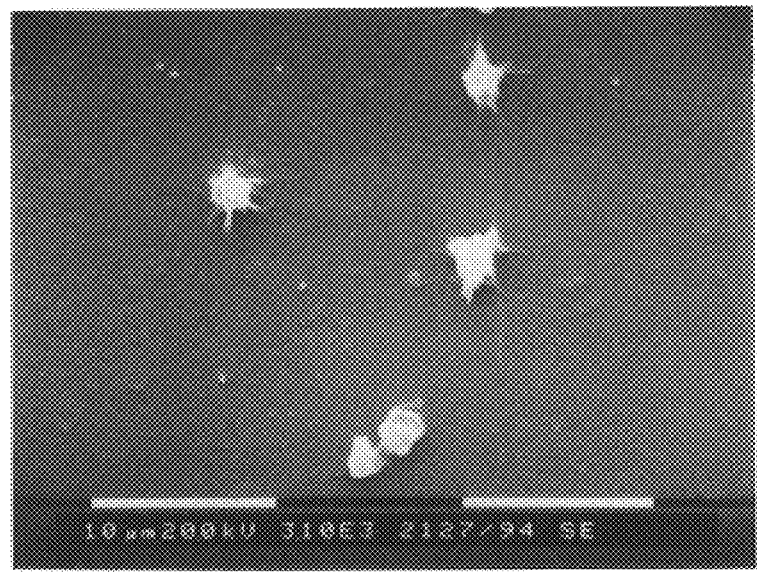
FIG. 2(D) is a SEM micrograph showing platelet adhesion on the surface of urethane-styrene IPN synthesized from a mixture of polyethylene glycol 1000 and polytetramethylene ether glycol 1000 (0:1).

FIGS. 1(A) to 1(C) are SEM micrographs showing platelet adhesion on the surface of IPN whose mean chain length (Mc) between chains are 1,800, 1,300 and 800, respectively. As shown in FIGS. 1(A) to 1(C), it is demonstrated that adhesion or modification of platelet remarkably decrease, as cross-linking density increases (i.e., as mean chain length shortens). Accordingly, it can be concluded that blood compatibility of urethane-styrene IPN can be dramatically improved by increasing cross-linking density.

EXAMPLE 7

Change of Blood Compatibility Depending on the Hydrophilicity of Urethane or Urethane-System IPN Urethane-styrene IPN was prepared in an analogous manner as in Example 6, after synthesizing polyurethane by preparing urethane prepolymer by employing a mixture of PEG with a molecular weight of 1000 and PTMG with a molecular weight of 1000 at a weight ratio of 1:0, 2:1, 1:2 and 0:1, by mixing this prepolymer and a mixture of TMP/1,4-butanediol (equivalent ratio=4:1) at an equivalent ratio of 1:1 and adding 0.05 wt % of T-12.

The blood compatibility of the resulted specimen was evaluated by platelet adhesion test and results are shown in FIGS. 2(A) to 2(D).

FIGS. 2(A) to 2(D) are SEM micrographs showing platelet adhesion on the surface of urethane-styrene IPN synthesized from a mixture of PEG 1000 and PTMG 1000 at a ratio of 1:0, 2:1, 1:2 and 0:1, respectively. As shown in FIGS. 2(A) to 2(D), it is demonstrated that adhesion or modification of platelet remarkably decrease, as the composition ratio of hydrophilic PEG decreases and the composition ratio of hydrophobic PTMG increases. Accordingly, it can be concluded that blood compatibility of urethane-styrene IPN can be improved by increasing the hydrophobicity of the urethane components.

As clearly illustrated and demonstrated as above, the present invention provides a method for improving blood compatibility of a synthesized IPN by controlling composition ratio of components, synthetic temperature, synthetic pressure, cross-linking density, hydrophobicity of polyurethane to inhibit phase separation of macromolecular mixture, while synthesizing IPN by cross-linking of hydrophilic urethane resin and hydrophobic styrene derivative. IPN materials of the invention may be widely used in various applications such as artificial organ or surface finishing material which are in direct contact with blood, since it inhibit thrombogenesis by suppressing platelet adhesion and agglutination.

Although the preferred embodiments of the present invention have been disclosed for illustrative purpose, those who are skilled in the art will appreciate that various modifications, additions and substitutions are possible, without departing from the scope and spirit of the invention as disclosed in the accompanying claims.

What is claimed is:

1. A method for improving blood compatibility of an interpenetrating polymer network (IPN) comprising a first macromolecule and a second macromolecule physically interwound together, the method comprising controlling domain size and inhibiting phase separation of a macromolecular mixture while synthesizing an IPN, wherein the first macromolecule is formed by polymerizing and cross-linking a hydrophilic urethane resin represented as the following formula (I) and the second macromolecule is formed by polymerizing and cross-linking a hydrophobic styrene derivative represented as the following formula (II) wherein at least some of the polymerization of one of the macromolecules occurs in the presence of the other macromolecule:

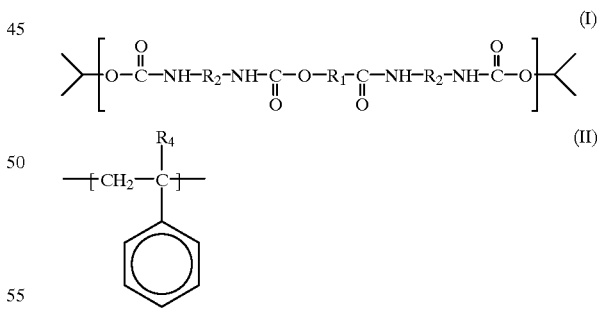

wherein $R_1$ is —[—$CHR_3$—$CH_2$—)$_n$—O—]$_m$(where, $R_3$ is hydrogen or methyl; n is an integer of 1 to 3; and m is an integer of 4 to 40);

$R_2$ is —(—CH—)$_n$—(where, n is an integer of 2 to 8); and $R_4$ is hydrogen or methyl, wherein a mean chain length between cross-linked chains of the first macromolecules is adjusted to be 800–1800, and wherein a mean chain length between cross-linked chains of the second macromolecules is adjusted to be 800–1800, wherein occlusion time is improved in an ex vivo A-A shunt test compared to a reference IPM produced in the same manner, except having a mean chain length less than 800.

2. The method for improving blood compatibility of an IPN of claim 1, wherein the interpenetrating polymer network is synthesized by fabricating simultaneously polyurethane and polystyrene network at a temperature range of 40 to 150° C.

3. The method for improving blood compatibility of an IPN of claim 1, wherein the interpenetrating polymer network is synthesized to contain 20 to 80 wt % of polyurethane network.

4. The method for improving blood compatibility of an IPN of claim 1, wherein the interpenetrating polymer network is synthesized by fabricating polystyrene network after fabricating polyurethane network.

5. The method for improving blood compatibility of an IPN of claim 4, wherein the polyurethane network is fabricated through UV photopolymerization at a temperature range of −40 to 50° C.

6. The method for improving blood compatibility of an IPN of claim 1, wherein the controlling of domain size and inhibition of phase separation are carried out at a polymerization pressure of 1 to 10,000 atmosphere pressure.

7. The method for improving blood compatibility of an IPN of claim 1, wherein the controlling of domain size and inhibition of phase separation are carried out by increasing hydrophobicity of polyurethane network by introducing more than two kinds of $R_1$ substituents having different hydrophilicity.

8. A n interpenetrating polymer network (IPN) comprising:

a hydrophilic macromolecule formed of a cross-linked urethane resin with a mean chain length of 800–1800 between cross-linked chains, the urethane being represented by Formula (I) and

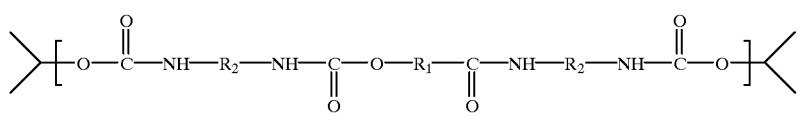

a hydrophobic macromolecule formed of a cross-linked styrene derivative, the styrene derivative being represented by Formula (II), wherein at least some of the polymerization of one of the macromolecules occurs in the presence of the other macromolecule; and

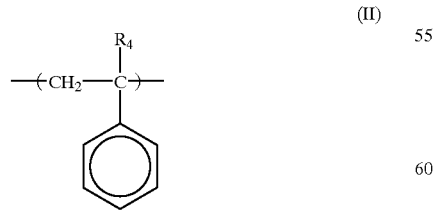

wherein $R_2$ is $-[-CHR_3-CH_2-)_n-O-]_m$ (where, $R_3$ is hydrogen or methyl; n is an integer of 1 to 3; and m is an integer of 4 to 40);

$R_2$ is $-(CH-)_n-$ (where, n is an integer of 2 to 8); and $R_4$ is hydrogen or methyl, wherein the hydrophilic macromolecule and the hydrophobic macromolecule are physically interwound with each other to form the interpenetrating polymer network, wherein occlusion time is improve din an ex vivo A-A shunt test compared to a reference IPN produced in the same manner, except having a mean chain length less than 800.

9. A blood compatible medical material comprising an interpenetrating polymer network of claim 8.

10. A medical device comprising a part contacting blood, the blood-contacting part is made of a material comprising an interpenetrating polymer network of claim 8.

11. A medical device as defined in claim 10, wherein the blood-contacting part comprises an artificial vein.

12. A method for making a medical device comprising a pat contacting blood, the blood-contacting part is made of a material comprising an interpenetrating polymer network of claim 8.

13. A method for making a blood compatible medical material, the method comprising:

polymerizing and cross-linking urethane resin represented by Formula (I) to form a hydrophilic macromolecule with a mean chain length of 800–1800 between cross-linked chains and

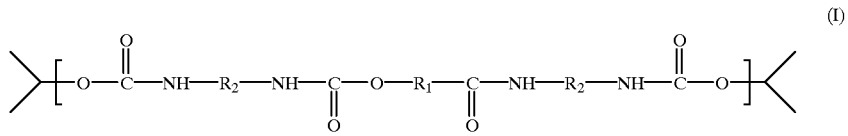
(I)

polymerizing and cross-linking styrene derivative represented by Formula (II) to form a hydrophobic macromolecule with a mean chain length of 800–1800 between cross-linked chains wherein at least some of the polymerization of one of the macromolecules occurs in the presence of the other macromolecule:

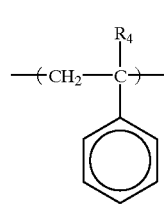
(II)

wherein, $R_1$ is $-[-(CHR_3-CH_2-)_n-O-]_m-$ (where, $R_c$ is hydrogen or methyl; n is an integer of 1 to 3; and m is an integer of 4 to 40);

$R_2$ is $-(-CH-)_n-$ (where, n is an integer of 2 to 8); and R4 is hydrogen or methyl wherein the hydrophilic and hydrophobic macromolecules are physically interwound with each other to form an interpenetrating polymer network (IPN), and phase separation between the hydrophilic and hydrophobic macromolecules occurs and forms domains in the IPN, wherein occlusion time is improved in an ex vivo A-A shunt test compared to a reference IPN produced in the same manner, except having a mean chain length less than 800.

14. A method as defined in claim 13, wherein size of the domains are controlled and the phase separation is inhibited during the formation of the hydrophilic and the hydrophobic macromolecules.

15. A method as defined in claim 13, wherein the domain size control and the inhibition of the phase separation is carried out by controlling polymerization pressure to 1 to 10,000 atm.

16. A method as defined in claim 13, wherein the domain size control and the inhibition of the phase separation is carried out by introducing more than two kinds of $R_1$ substituents having different hydrophobicity.

* * * * *

UNITED STATES PATENT AND TRADEMARK OFFICE
CERTIFICATE OF CORRECTION

PATENT NO. : 6,156,344
DATED : December 5, 2000
INVENTOR(S) : S. Kim, et. al.

It is certified that error appears in the above-identified patent and that said Letters Patent is hereby corrected as shown below:

Column 9, Line 64, "$R_2$" should be changed to "$R_1$".

Column 10, Line 6, "improve din" should be "improved in".

Column 10, Line 26, "pat" should be changed to "part".

Column 11, Line 27, "$R_C$" should be changed to "$R_3$".

Signed and Sealed this

First Day of May, 2001

Attest:

NICHOLAS P. GODICI

Attesting Officer     *Acting Director of the United States Patent and Trademark Office*